United States Patent
Sakai et al.

(12)

(10) Patent No.: US 6,187,921 B1
(45) Date of Patent: Feb. 13, 2001

(54) 2-AMINO-6-CHLOROPURINE AND METHOD FOR PREPARING THE SAME

(75) Inventors: Masatoshi Sakai; Masaki Fujiwara; Toshio Nakamatsu, all of Kurashiki (JP)

(73) Assignee: Sumika Fine Chemicals Co., Ltd., Osaka (JP)

( * ) Notice: Under 35 U.S.C. 154(b), the term of this patent shall be extended for 0 days.

(21) Appl. No.: 09/104,192

(22) Filed: Jun. 25, 1998

Related U.S. Application Data

(62) Division of application No. 08/741,223, filed on Oct. 29, 1996, now Pat. No. 5,789,590.

(30) Foreign Application Priority Data

Nov. 9, 1995 (JP) .................................................. 7-317204

(51) Int. Cl.⁷ .................................................. C07D 473/40
(52) U.S. Cl. .................................................. 544/277
(58) Field of Search ............................................. 544/277

(56) References Cited

U.S. PATENT DOCUMENTS

| 2,815,346 | * | 12/1957 | Hitchings | 544/277 |
| 4,736,029 | * | 4/1988 | Harnder | 544/277 |
| 5,389,637 | * | 2/1995 | Igi | 544/277 |

FOREIGN PATENT DOCUMENTS

| 4415196 | * | 4/1995 | (DE) . |
| 415196 | | 4/1995 | (DE) . |
| 4342131 | * | 6/1995 | (DE) . |
| 0543095 | | 5/1993 | (EP) . |
| 543095 | * | 5/1993 | (EP) . |
| 590361 | * | 9/1993 | (EP) . |
| 7-300480 | * | 11/1995 | (JP) . |
| 7300480 | | 11/1995 | (JP) . |
| 92-13859 | * | 8/1992 | (WO) . |
| 93/15075 | * | 8/1993 | (WO) . |
| WO93/15075 | | 8/1993 | (WO) . |
| WO94/07892 | | 4/1994 | (WO) . |
| 94/07892 | * | 4/1994 | (WO) . |

OTHER PUBLICATIONS

Nasutavicus, J. Het Chem 11, 77, 1974.*
Davies, JACS 82, 2633, 1960.*
Abstract of DE 4231036 (A1).
Abstract of WO93/15075.
Abstract of JP–5–213952 (A2).
Abstract of DE 4142568 (A1).
Abstract of EP 543095 (A2).
Abstract of WO92/13859.
Abstract of Shengwu Huaxue Yu Shengwu Wuli Jinzhan (1987)(2)62–4.
Abstract of JP–61–227583 (A2).
Abstract of J. Heterocycl. Chem. (1974) 11(1) 77–8.
Davies, G.D. et al., J. Am. Chem. Sol., 82, 2633–2640 (May 20, 1960).
Nasutovicus, J. Het. Chem. 77–8(1974).

* cited by examiner

*Primary Examiner*—Mark L. Berch
(74) *Attorney, Agent, or Firm*—Birch, Stewart, Kolasch & Birch, LLP

(57) ABSTRACT

2-Amino-6-chloropurine having a double cone-like crystal form.

2 Claims, 6 Drawing Sheets

50 μm

50 μm

2-AMINO-6-CHLOROPURINE AND METHOD FOR PREPARING THE SAME

This application is a divisional of Application Ser. No. 08/741,223, filed on Oct. 29. 1996 U.S. Pat. No. 5,789,590, the entire contents of which are hereby incorporated by reference.

BACKGROUND OF THE INVENTION

1. Field of the Invention

The present invention relates to 2-amino-6-chloropurine and to a method for preparing the same. More specifically, the present invention relates to 2-amino-6-chloropurine having a double cone-like crystal form, which is useful as an intermediate for the preparation of an antiviral agent and to a method for preparing the same.

2. Discussion of Related Art

Conventional 2-amino-6-chloropurine has a very fine acicular (needle-like) or irregular-shaped crystal form.

As a method for preparing 2-amino-6-chloropurine, there has been known a method comprising neutralizing an alkaline hydrolysis solution of 2-formylamino-6-chloropurine with an acid as disclosed in JP-A-6-157530.

The above known method, however, has a defect that the resulting amino-6-chloropurine is contaminated with impurities generated during its synthesis, which deteriorates the quality of a product.

Also, since the 2-amino-6-chloropurine prepared by the above known method is very fine crystal, it has arisen some problems such as poor filtration efficiency, coagulation upon drying and the necessity of long period of time for drying. Moreover, the 2-amino-6-chloropurine necessitates troublesome procedures such as grinding upon its use, and, therefore, impairs the productivity of a final product.

An object of the present invention is to provide 2-amino-6-chloropurine having a high purity.

Another object of the present invention is to provide 2-amino-6-chloropurine containing little impurities and hardly coagulating upon drying after its synthesis.

These and other objects of the present invention will be apparent from the following description.

SUMMARY OF THE INVENTION

In accordance with the present invention, there are provided 2-amino-6-chloropurine having a double cone-like crystal form, and a method for preparing 2-amino-6-chloropurine having a double cone-like crystal form, which comprises suspending 2-amino-6-chloropurine having an acicular or irregular-shaped crystal form in water having a pH of from 3 to 10 and heating the resulting suspension.

DETAILED DESCRIPTION OF THE INVENTION

Figure 1:
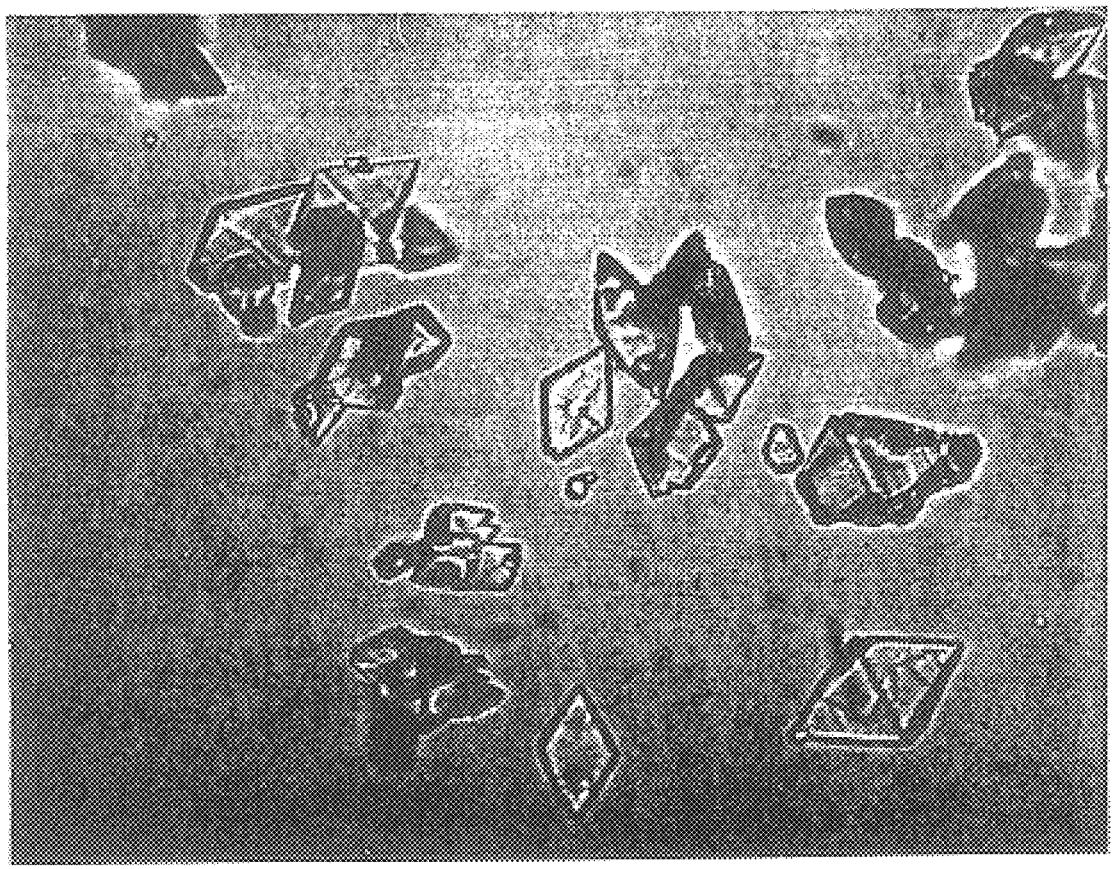
FIG. 1 is a microscopic photograph showing crystals of 2-amino-6-chloropurine having a double cone-like crystal form obtained in Example 1.

According to the method for preparing 2-amino-6-chloropurine having a double cone-like crystal form of the present invention, 2-amino-6-chloropurine can be obtained in a higher purity and easily separated from the reaction solution by filtration in comparison with the conventional method for preparing 2-amino-6-chloropurine having an acicular or irregular-shaped crystal form. Therefore, the method according to the present invention is very advantageous with respect to productivity of industrial synthesis as compared with the conventional method.

The 2-amino-6-chloropurine of the present invention has a novel double cone-like crystal form at a glance when microscopically observed, and the crystals of the present invention usually has an average particle diameter of 60 to 66 $\mu$m as determined by the laser light diffraction and scattering methods using SALD-1100 manufactured by Shimadzu Co., Ltd.

The 2-amino-6-chloropurine of the present invention exactly has such a crystal form constructed by combining two polygonal pyramids with each other at their bottom faces such as polygonal bipyramid.

Owing to the difference in crystal form as demonstrated above, 2-amino-6-chloropurine of the present invention is more easily filtered off from the reaction solution after its synthesis and more readily dried after filtration, as compared with the conventional crystals.

2-Amino-6-chloropurine of the present invention is powder having excellent fluidity, and does not coagulate unlike 2-amino-6-chloropurine having a very fine acicular or irregular-shaped crystal form. Therefore, grinding and other troublesome procedures are not necessitated for the 2-amino-6-chloropurine of the present invention after its preparation. These effects endowed by the crystal form of the present invention advantageously improve the productivity in industrial scale production.

2-Amino-6-chloropurine having a double cone-like crystal form can be obtained by suspending 2-amino-6-chloropurine having an acicular or irregular-shaped crystal form produced by a conventional method in water within the pH range of 3 to 10 and heating the resulting suspension.

The 2-amino-6-chloropurine having an acicular or irregular-shaped crystal form can be prepared by hydrolyzing 2-formylamino-6-chloropurine or a salt thereof in water in the presence of an acid or an alkali, followed by neutralizing the resulting reaction mixture. For example, the 2-amino-6-chloropurine having an acicular or irregular-shaped crystal form can be produced by a conventional method as disclosed in JP-6-157530. Specifically, dimethylformamide, phosphorus oxychloride and guanine are added to 1,2-dichloroethane, and the mixture is stirred with heating. After cooling, the reaction mixture is added to water, to which sodium carbonate is added to adjust the pH of the mixture to 4. Then, the aqueous layer is separated therefrom, which is then neutralized by adding sodium hydroxide thereto. The precipitated crystal of 2-dimethylaminomethyleneamino-6-chloropurine is filtered off and added to an aqueous solution of acetic acid. The solution is stirred with heating to precipitate crystals. The precipitated crystals are filtered off and washed with water to give crystals of 2-formylamino-6-chloropurine acetate. The crystals of 2-formylamino-6-chloropurine acetate are then dissolved in an aqueous solution of a metal hydroxide such as sodium hydroxide with stirring. The solution is neutralized with hydrochloric acid, acetic acid or sulfuric acid to precipitate crystals. The precipitated crystals are filtered off to obtain acicular or irregular-shaped white crystals of 2-amino-6-chloropurine.

The pH of water, in which 2-amino-6-chloropurine having an acicular or irregular-shaped crystal form is suspended, is not higher than 10, preferably not higher than 9.5 from the viewpoint of facilitating the dissolution of 2-amino-6-chloropurine and the conversion of crystal form from an acicular or irregular-shaped form to a double cone-like form (hereinafter simply referred to as "crystal-form conversion"); and not lower than 3, preferably not lower than 7 from the viewpoint of preventing the hydrolysis of 2-amino-6-chloropurine.

The heating temperature is not lower than 70° C., preferably not lower than 85° C. from the viewpoint of the crystal-form conversion; and not higher than 100° C., preferably not higher than 90° C. from the viewpoint of preventing decomposition of the resulting 2-amino-6-chloropurine. The heating period of time is not particularly limited and appropriately adjusted to the period of time necessary for the completion of the crystal-form conversion. It usually takes about 1 to 30 minutes for the crystal-form conversion.

The crystal-form conversion can be carried out in a reaction system under atmospheric pressure or under increased pressure. When the conversion is carried out under increased pressure, the pressure applied to the reaction system is preferably not higher than about 5 kg/cm$^2$.

Alternatively, the process for isolating the 2-amino-6-chloropurine having an acicular or irregular-shaped crystal form may be omitted. In this case, the reaction mixture, where 2-amino-6-chloropurine having an acicular or irregular-shaped crystal form has been precipitated, is adjusted to a pH of from 3 to 10 and then heated. Here, it is desired that the heating is carried out at a temperature of from 70° to 100° C., preferably 85° to 100° C. for 1 to 30 minutes.

After the completion of the crystal-form conversion, from the viewpoint of achieving high yield and high quality, it is desired that 2-amino-6-chloropurine crystals are quenched rapidly to 50° C. or lower, filtered off, and washed with water or methanol. The 2-amino-6-chloropurine thus obtained is dried to give powdery 2-amino-6-chloropurine having a double cone-like crystal form of the present invention.

EXAMPLES

The present invention is hereinafter described in more detail by means of the following working examples, which are not to be construed as limitative.

Example 1

To 500 ml of 1,2-dichloroethane, 131.6 g (1.8 moles) of N,N-dimethylformamide and 138.0 g (0.9 moles) of phosphorus oxychloride were added, and 45.3 g (0.3 moles) of guanine was then added to the mixture, followed by stirring at 80° C. for 8 hours.

After the reaction mixture was cooled to 30° C., the reaction mixture was added to 1200 ml of water, which was then adjusted to pH 4 by adding 175.6 g (1.65 moles) of sodium carbonate.

After 30-minute stirring, the reaction mixture was kept standing to separate the aqueous layer therefrom. To the aqueous layer separated, 25.2 g (0.63 moles) of sodium hydroxide was slowly added.

From the reaction mixture, 60.7 g (0.27 moles) of crystals of 2-dimethylaminomethyleneamino-6-chloropurine was obtained.

Then, 60.7 g of the crystals of 2-dimethylaminomethyleneamino-6-chloropurine obtained were added to 650 ml of a 12% by weight acetic acid aqueous solution and stirred at 70° C. for 3 hours. Next, the reaction mixture was cooled to 25° C., and the crystals of 2-formylamino-6-chloropurine acetate were filtered off and washed with water.

The resulting crystals of 2-formylamino-6-chloropurine acetate were dried.

A 55.6g (0.216 moles) aliquot of the 2-formylamino-6-chloropurine acetate crystals obtained was dissolved in 370 ml of a 10% by weight sodium hydroxide aqueous solution and stirred at room temperature for 2 hours, to which 14.5 g of active carbon was added and stirred for 1 hour. The active carbon was removed from the solution by filtration to give a 2-amino-6-chloropurine reaction solution. Then, the reaction solution was neutralized with 35% hydrochloric acid to obtain slurry of crystallized 2-amino-6-chloropurine.

The pH of the slurry of the crystallized 2-amino-6-chloropurine thus obtained was adjusted to 7 and heated up to 85° C. After the heating temperature attained to 85° C., the slurry was quenched rapidly to room temperature to precipitate crystals. The crystals precipitated were filtered off using filter paper No. 2 having a diameter of 9 cm under reduced pressure of 20 to 30 mmHg. It took about 35 seconds to filter off the crystals. Then, the crystals were washed with water to obtain 2-amino-6-chloropurine crystals in a wet state. The crystals were dried at 50° C. under reduced pressure using an evaporator.

The resulting crystals weighed 33.5 g (0.198 moles), and had an average particle diameter of 60 μm. The crystals did not show coagulation, and showed excellent fluidity.

The yield of the 2-amino-6-chloropurine was 91.7% by weight based upon the amount of 2-formylamino-6-chloropurine acetate used.

The crystals of 2-amino-6-chloropurine were observed by means of an optical microscope. FIG. 1 is a microscopic photograph of the crystals (magnification: ×400).

The properties of the 2-amino-6-chloropurine thus obtained were examined in accordance with the following methods. The analysis of HPLC (high performance liquid chromatography) was carried out by means of LC-10A manufactured by Shimadzu Co., Ltd. (Column: TSK-gel ODS-80TM, 15 cm×4.6 mmΦ manufactured by Toso Co., Ltd.; Mobile phase: Aqueous buffer/methanol=75/25, flow rate:1.0 ml/min, wavelength: 254 nm). Also, the analysis of H-NMR was carried out by means of JMN-EX270 manufactured by JEOL Co., Ltd. The results are as follows:

Results of HPLC: The retention time of the obtained compound was about 5.4 minutes, which was consistent with the retention time of a known 2-amino-6-chloropurine.

$^1$H-NMR(CD$_3$)$_2$SO)δ(ppm): 6.75, 8.08, 12.80
These values are also consistent with 2-amino-6-chloropurine having an acicular or irregular-shaped crystal form.

From the above results, the obtained compound was identified as 2-amino-6-chloropurine.

Also, the purity of the 2-amino-6-chloropurine obtained was determined. The results are shown in Table 1.

The 2-amino-6-chloropurine obtained was subjected to a powder X-ray diffraction analysis under the following conditions:

Target: Cu
Filter: Not used
Voltage: 50 kV
Current: 300 mA
X-ray: CuKα-ray

Figure 3:
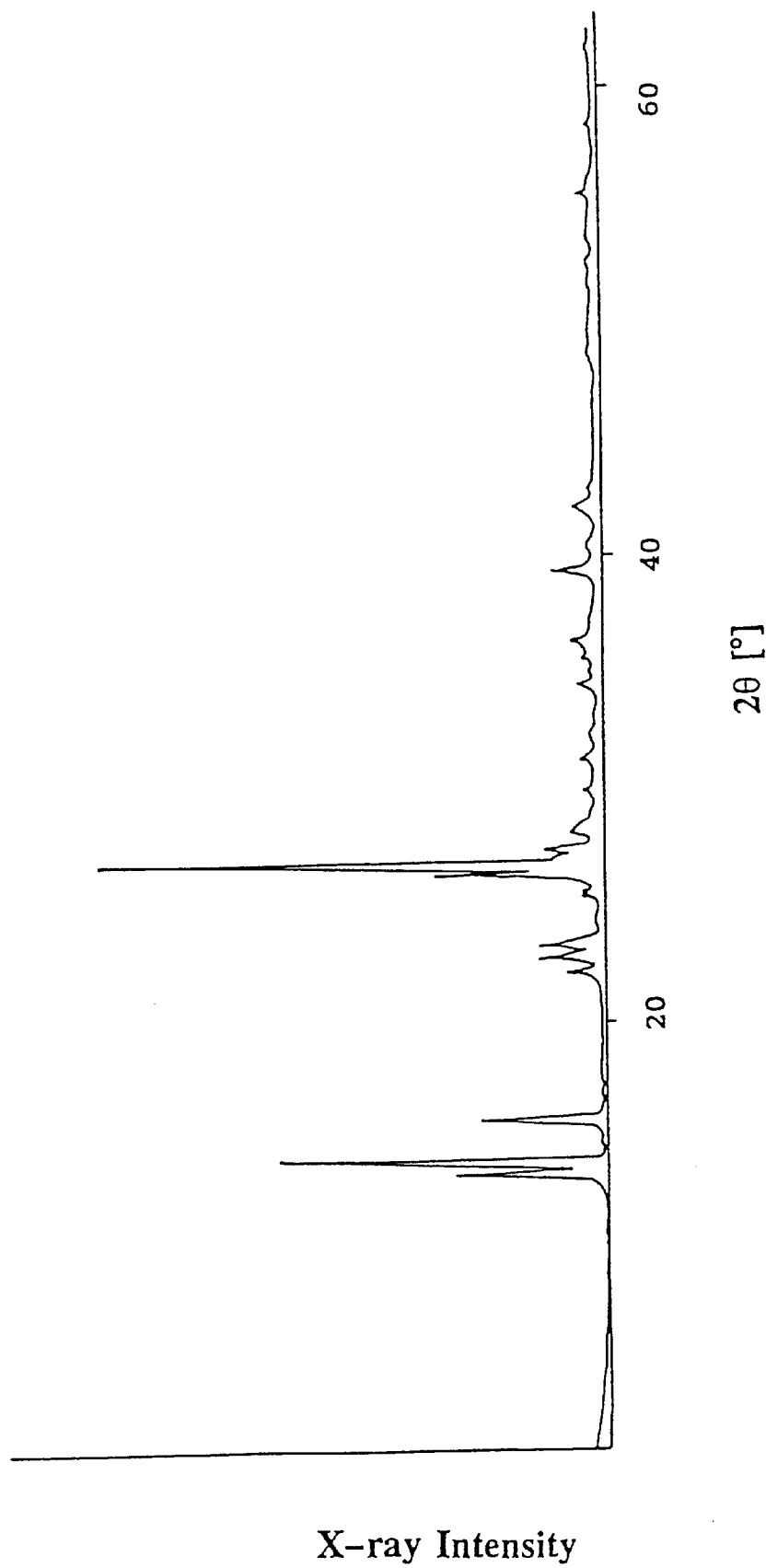
FIG. 3 shows a powder X-ray diffraction pattern of crystals of 2-amino-6-chloropurine having a double cone-like crystal form obtained in Example 1.
Figure 5:
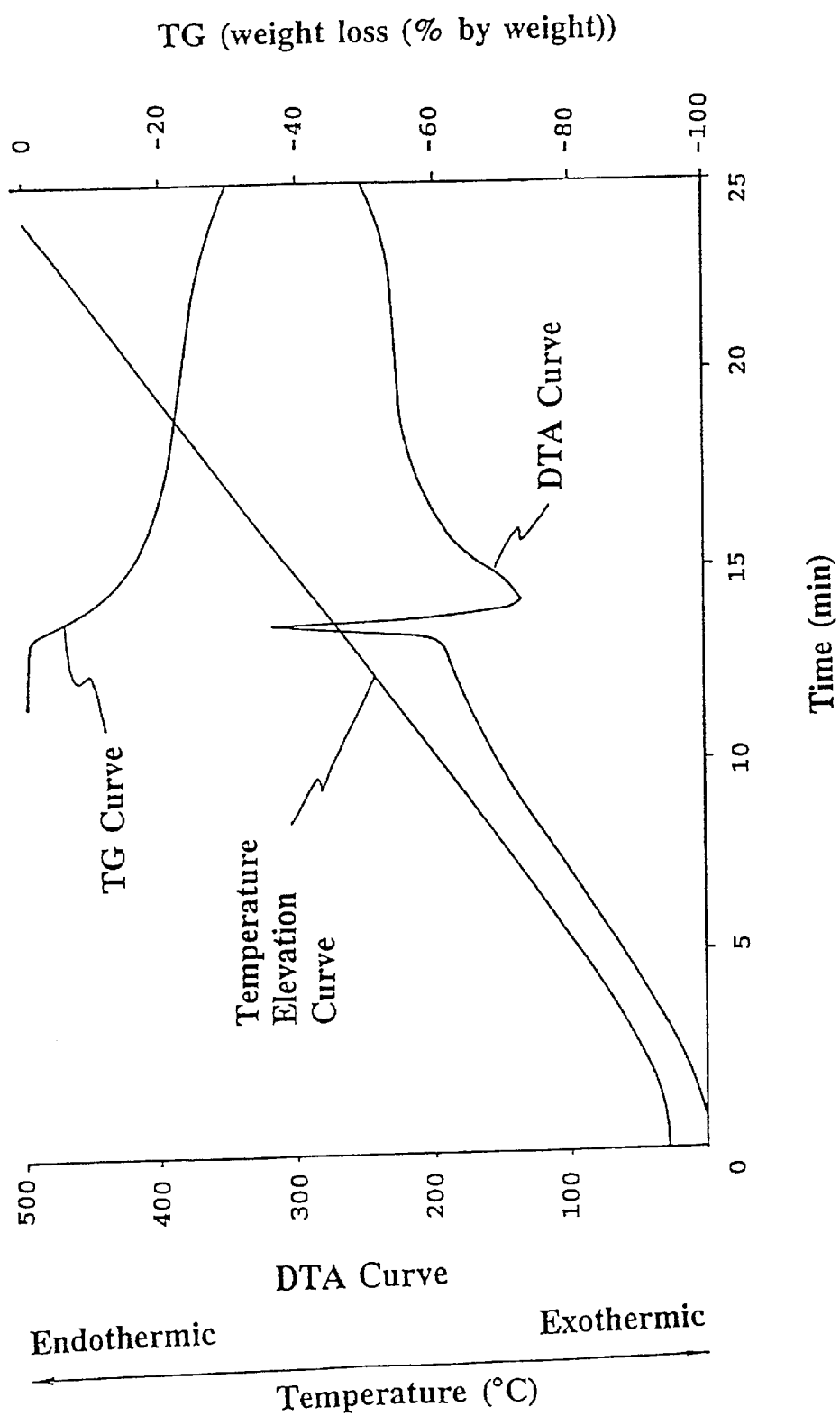
FIG. 5 shows the results of differential thermal analysis (DTA) and thermogravimetry (TC) of crystals of 2-amino-6-chloropurine having a double cone-like crystal form obtained in Example 1.

The results are shown in FIG. 3. As is clear from the results shown in FIG. 3, the 2-amino-6-chloropurine shows relatively high X-ray intensities at 2θ=13.6° and 2θ=26.4°, which indicates that its crystal structure is different from that of the conventional 2-amino-6-chloropurine. Also, the difference of crystal structure was confirmed by differential thermal analysis (DTA) and thermogravimetry (TG) using TG/DTA 200 manufactured by Seiko Instruments Inc. The results are shown in FIG. 5.

Comparative Example 1

Crystals of 2-formylamino-6-chloropurine acetate were prepared in the same manner as in Example 1.

The crystals obtained in an amount of 60.7 g were dissolved in 408 g of a 10% by weight sodium hydroxide aqueous solution and stirred at room temperature for 2 hours. Then, the mixture was neutralized with 35% hydrochloric acid to precipitate crystals. The precipitated crystals were filtered off using filter paper No. 2 having a diameter of 9cm under reduced pressure of 20 to 30 mmHg, washed with water to obtain 35.6 g (0.21 moles) of white crystals of 2-amino-6-chloropurine. It took about 4.5 minutes to filter off the crystals, which is much longer than that required for filtration of the double cone-like crystals obtained in Example 1. The yield based upon the amount of guanine was 70% by weight.

When white crystals obtained were dried at 50° C. under reduced pressure of 20 to 30 mmHg, coagulation of the crystals was observed. The crystals had an average length of 15 μm.

The yield and purity of the 2-amino-6-chloropurine obtained were determined in the same manner as those in Example 1. The results are shown in Table 1.

Figure 2:
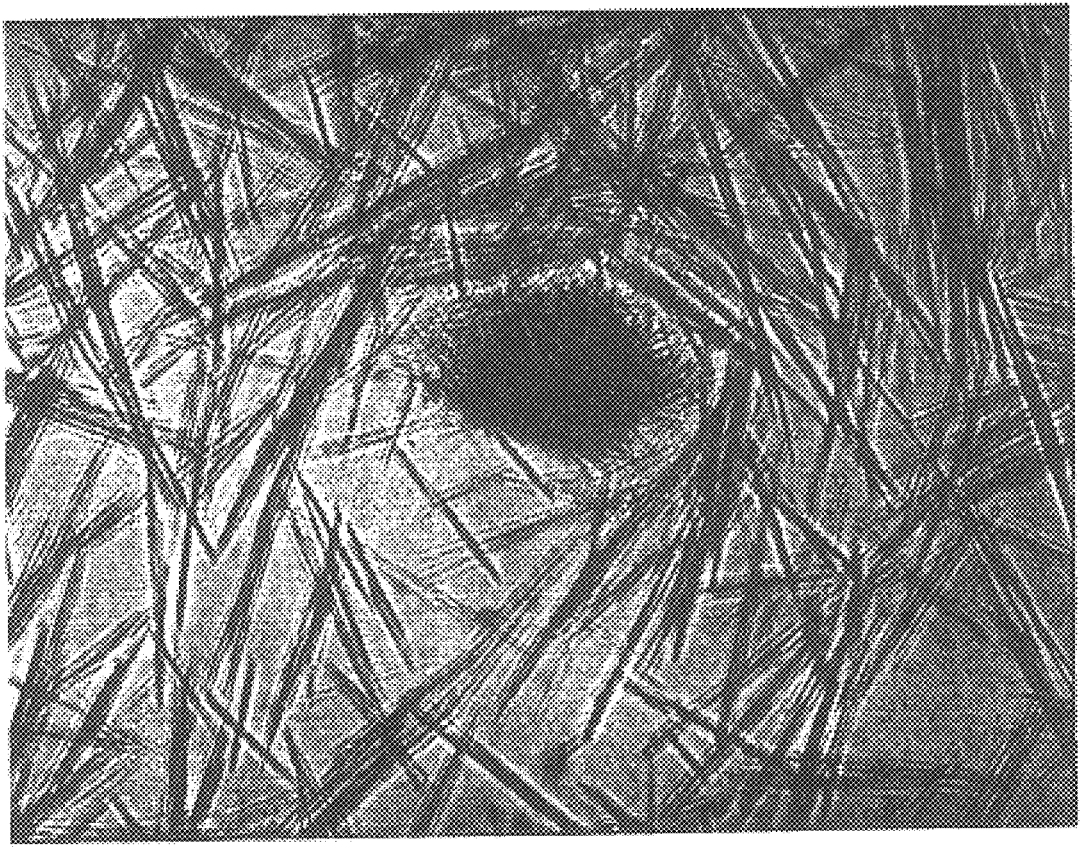
FIG. 2 is a microscopic photograph showing crystals of 2-amino-6-chloropurine obtained in Comparative Example 1.

The crystals of 2-amino-6-chloropurine were observed by means of an optical microscope. FIG. 2 is a microscopic photograph of the crystals (magnification: ×400).

The powder X-ray diffraction patterns of the crystals of 2-amino-6-chloropurine obtained in Comparative Example 1 were examined in the same manner as in Example 1. The results are shown in FIG. 4.

The crystals of 2-amino-6-chloropurine obtained in Comparative Example 1 were subjected to differential thermal analysis (DTA) and thermogravimetry (TG) in the same manner as in Example 1. The results are shown in FIG. 6.

As is clear from the comparison of FIG. 1 with FIG. 2, the 2-amino-6-chloropurine obtained in Example 1 has a double cone-like crystal form which is quite different from the acicular crystal form of the conventional 2-amino-6-chloropurine obtained in Comparative Example 1. Also, the 2-amino-6-chloropurine having a double cone-like crystal form of the present invention shows mechanical strength higher than the conventional 2-amino-6-chloropurine having an acicular crystal form. Therefore, the crystals of 2-amino-6-chloropurine of the present invention are hardly crushed into fine splinters. Accordingly, pores of a filter are hardly obstructed by the crystals. In other words, the 2-amino-6-chloropurine crystals of the present invention brings good filtration efficiency to a filter, thereby advantageous effects such as easiness in handling can further be exhibited. These effects achieved by the present invention are industrially very advantageous.

Figure 4:
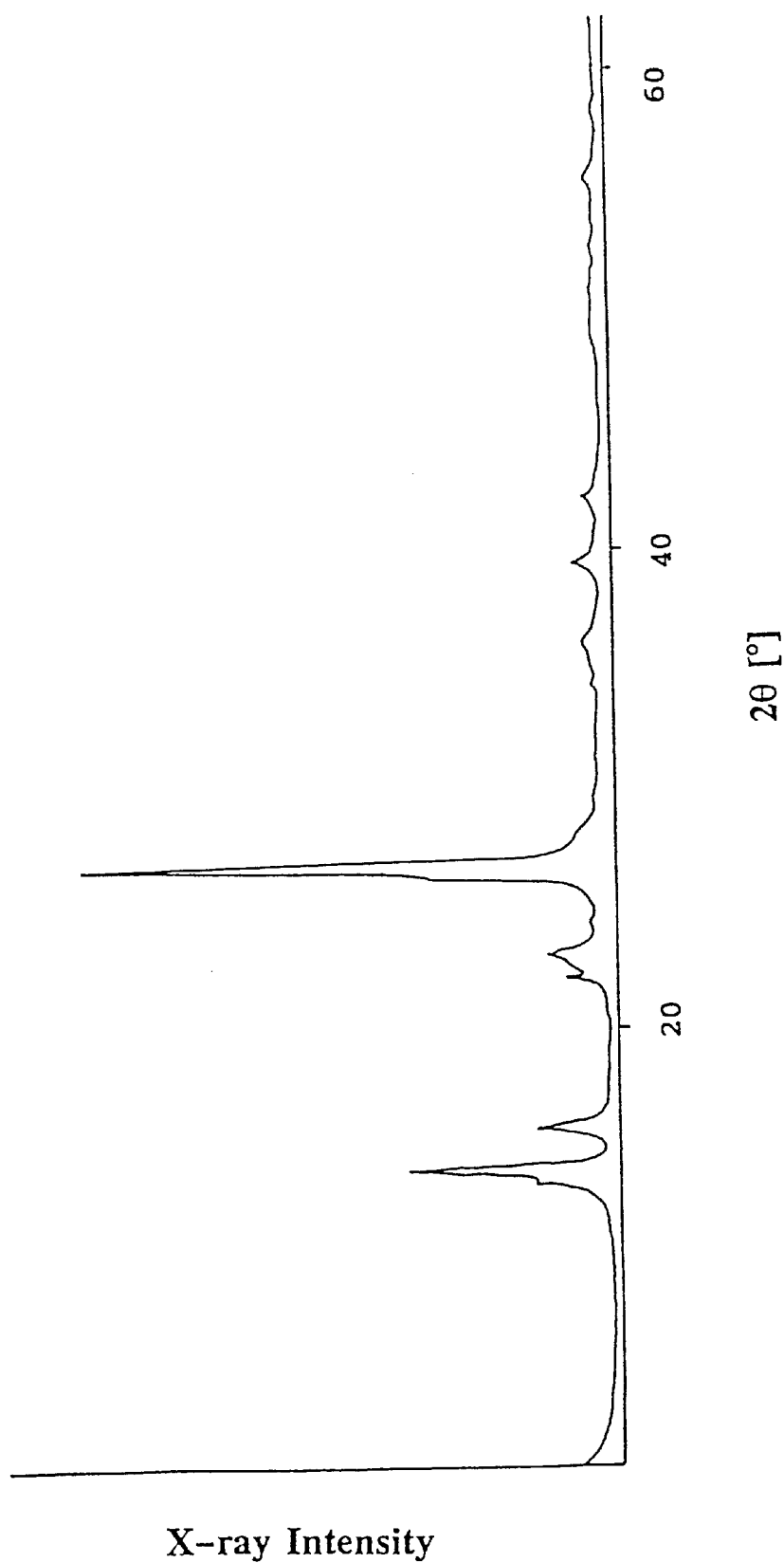
FIG. 4 shows a powder X-ray diffraction pattern of crystals of 2-amino-6-chloropurine obtained in Comparative Example 1.

The comparison of the powder X-ray diffraction patterns of FIG. 3 with that of FIG. 4 indicates that the crystals of 2-amino-6-chloropurine obtained in Example 1 are distinctly different from the crystals obtained in Comparative Example 1. Indeed, the crystals obtained in Example 1 show relatively high X-ray intensities at 13.6° and 26.4°, while the crystals obtained in Comparative Example 1 do not show such intensities at these angles.

Figure 6:
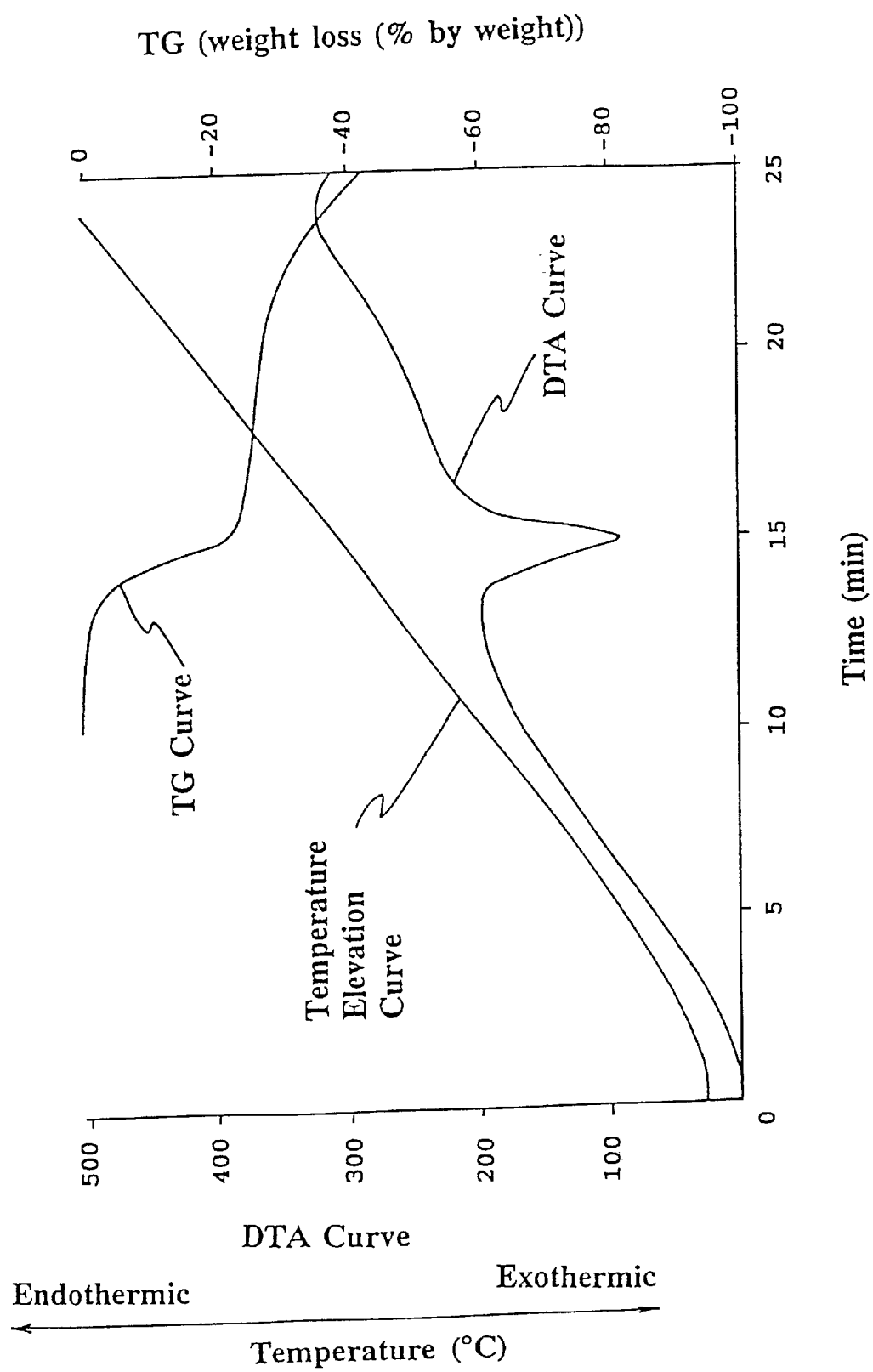
FIG. 6 shows the results of differential thermal analysis (DTA) and thermogravimetry (TG) of crystals of 2-amino-6-chloropurine obtained in Comparative Example 1.

From the results of the DTA and TG shown in FIG. 5 and 6, it can be seen that there is a distinct difference between the crystals of 2-amino-6-chloropurine obtained in Example 1 and Comparative Example 1. That is, exothermic and endothermic reactions occurred in the crystals obtained in Example 1 at 273.1° C. and 284.1° C., respectively, whereas only endothermic reaction occurred in the crystals obtained in Comparative Example 1 at 301.8° C.

Example 2

2-Amino-6-chloropurine was prepared in the same manner as in Example 1 except that sulfuric acid was used instead of hydrochloric acid for neutralization.

The analyses of crystal form and properties of the 2-amino-6-chloropurine thus obtained were carried out in the same manner as in Example 1. As a result, it was confirmed that the 2-amino-6-chloropurine obtained in Example 2 had the same crystal form and properties as those obtained in Example 1. The obtained crystals have an average particle diameter of 62 μm.

Next, the yield of 2-amino-6-chloropurine based upon the used amount of 2-formylamino-6-chloropurine acetate, and the purity of the resulting 2-amino-6-chloropurine were determined in the same manner as in Example 1. The results are shown in Table 1.

Example 3

2-Amino-6-chloropurine was prepared in the same manner as in Example 1 except that pH of the 2-amino-6-chloropurine slurry after neutralization was adjusted to 9.1.

The analyses of crystal form and properties of the 2-amino-6-chloropurine thus obtained were carried out in the same manner as in Example 1. As a result, it was confirmed that the 2-amino-6-chloropurine obtained in Example 3 had the same crystal form and properties as those obtained in Example 1. The obtained crystals have an average particle diameter of 60 μm.

Next, the yield of 2-amino-6-chloropurine based upon the used amount of 2-formylamino-6-chloropurine acetate, and the purity of the resulting 2-amino-6-chloropurine were determined in the same manner as in Example 1. The results are shown in Table 1.

TABLE 1

| Example No. | Yield (% by weight) | Purity (% by weight) |
| --- | --- | --- |
| 1 | 91.7 | 97.8 |
| 2 | 92.3 | 96.9 |
| 3 | 92.9 | 97.8 |
| Comparative Example 1 | 92.0 | 77.5 |

From the results shown in Table 1, it can be seen that all of the 2-amino-6-chloropurines obtained in Examples 1 to 3 were produced in a high yield with a low content of impurities.

Example 4

2-Amino-6-chloropurine was prepared in the same manner as in Example 1 except that acetic acid was used instead of hydrochloric acid to neutralize the reaction mixture.

The analyses of crystal form and properties of the 2-amino-6-chloropurine thus obtained were carried out in the same manner as in Example 1. As a result, it was confirmed that the 2-amino-6-chloropurine obtained in Example 4 had the same crystal form and properties as those obtained in Example 1. The obtained crystals have an average particle diameter of 63 $\mu$m.

The yield of 2-amino-6-chloropurine based upon the used amount of 2-formylamino-6-chloropurine acetate was 92.0% by weight. It was confirmed that the purity of the 2-amino-6-chloropurine was the same as that obtained in Example 1.

Example 5

2-Amino-6-chloropurine was prepared in the same manner as in Example 1 except that pH of the 2-amino-6-chloropurine slurry after neutralization was adjusted to 3.

The analyses of crystal form and properties of the 2-amino-6-chloropurine thus obtained were carried out in the same manner as in Example 1. As a result, it was confirmed that the 2-amino-6-chloropurine obtained in Example 5 had the same crystal form and properties as those obtained in Example 1. The obtained crystals have an average particle diameter of 60 $\mu$m.

The yield of 2-amino-6-chloropurine based upon the amount of 2-formylamino-6-chloropurine acetate was 92.0% by weight, and it was confirmed that the purity of the 2-amino-6-chloropurine was the same as that obtained in Example 1.

Example 6

2-Amino-6-chloropurine was prepared in the same manner as in Example 1 except that active carbon was used in an amount of 5% by weight of 2-formylamino-6-chloropurine acetate.

The analyses of crystal form and properties of the 2-amino-6-chloropurine thus obtained were carried out in the same manner as in Example 1. As a result, it was confirmed that the 2-amino-6-chloropurine obtained in Example 6 had the same crystal form and properties as those obtained in Example 1. The obtained crystals have an average particle diameter of 60 $\mu$m.

The yield of 2-amino-6-chloropurine based upon the amount of 2-formylamino-6-chloropurine acetate used was 94.0% by weight. It was confirmed that the purity of the 2-amino-6-chloropurine was the same as that obtained in Example 1.

Example 7

2-Amino-6-chloropurine was prepared in the same manner as in Example 1 except that active carbon was used in an amount of 10% by weight of 2-formylamino-6-chloropurine acetate.

The analyses of crystal form and properties of the 2-amino-6-chloropurine thus obtained were carried out in the same manner as in Example 1. As a result, it was confirmed that the 2-amino-6-chloropurine obtained in Example 7 had the same crystal form and properties as those obtained in Example 1. The obtained crystals have an average particle diameter of 65 $\mu$m.

The yield of 2-amino-6-chloropurine based upon the amount of 2-formylamino-6-chloropurine acetate was 92.8% by weight. It was confirmed that the purity of the 2-amino-6-chloropurine was the same as that obtained in Example 1.

The present invention being thus described, it will be obvious that the same may be varied in many ways. Such variations are not to be regarded as a departure from the spirit and scope of the present invention, all such modifications as would be obvious to one skilled in the art are intended to be included within the scope of the following claims.

What is claimed is:

1. 2-amino-6-chloropurine having a double cone-like crystal form constructed by combining two pyramids with each other at their bottoms and having an average particle diameter of 60 to 66 $\mu$m.

2. The 2-amino-6-chloropurine according to claim 1, wherein said 2-amino-6-chloropurine has an exothermic peak at about 273° C. when DTA is carried out.

* * * * *